United States Patent [19]

Paulos et al.

[11] Patent Number: 5,112,337
[45] Date of Patent: May 12, 1992

[54] VARIABLE ANGLE, SELECTIVE LENGTH TIBIAL DRILL GUIDE

[75] Inventors: Lonnie E. Paulos; E. Paul France, both of Salt Lake City; Richard L. Ellingson, Draper, all of Utah

[73] Assignee: DePuy Du Pont Orthopaedics, Warsaw, Ind.

[21] Appl. No.: 650,680

[22] Filed: Feb. 5, 1991

[51] Int. Cl.$^5$ .............................................. A11B 17/00
[52] U.S. Cl. ........................................ 606/96; 606/98
[58] Field of Search .................................. 606/96–100

[56] References Cited

U.S. PATENT DOCUMENTS

| | | |
|---|---|---|
| 4,312,337 | 1/1982 | Donohue . |
| 4,535,768 | 8/1985 | Hourahane et al. ............. 606/96 |
| 4,708,139 | 11/1987 | Dunbar ............................. 606/96 |
| 4,722,331 | 2/1988 | Fox .................................. 606/96 |
| 4,739,751 | 4/1988 | Sapega et al. ................... 606/96 |
| 4,772,286 | 9/1988 | Goble et al. ..................... 623/13 |
| 4,781,182 | 11/1988 | Purnell et al. ................... 606/96 |
| 4,834,080 | 5/1989 | Brown ............................. 606/98 |
| 4,862,882 | 9/1989 | Venturi et al. .................. 606/96 |
| 4,883,048 | 11/1989 | Purnell et al. ................... 606/96 |
| 4,911,153 | 3/1990 | Border ............................. 606/98 |

OTHER PUBLICATIONS

"Surgical Techniques", Arthrex Arthroscopy Instruments, Inc., pp. 1-38, 1991.
Purnell et al., "Arthroscopic Anterior Cruciate Ligament Reconstruction", Johnson & Johnson Orthopaedics, pp. 1-24, 1988.
T. Rosenberg, M.D., "Arthroscopic Technique for Anterior Cruciate Reconstruction", Acufex Microsurgical, Inc., 1988.
L. Paulos, M.D., "Concept Precise ACL Guide System", pp. 71, 95, Salt Lake City, Ut.

Primary Examiner—Stephen C. Pellegrino
Assistant Examiner—Gary Jackson
Attorney, Agent, or Firm—Barnes & Thornburg

[57] ABSTRACT

A drill guide for drilling a tunnel in a tibia for anterior cruciate ligament replacement comprises a target hook having a point for engaging and determining the exit of the tunnel in the tibial plateau, and a handle carrying a drill guide sleeve holder and selectively variable means for adjusting and rigidly fixing the angular position of the holder relative to the plateau. The drill guide also comprises a drill sleeve longitudinally selectively adjustably received in the holder for axial movement toward and away from the point, the drill sleeve having a proximal end extending toward the point. The drill sleeve is cannulated to receive a guide wire with a sharpened point headed toward the point. Engagement means for holding the drill sleeve in a selected position is provided, thereby preselecting the desired tunnel length defined between the proximal end of said drill sleeve and the point.

11 Claims, 2 Drawing Sheets

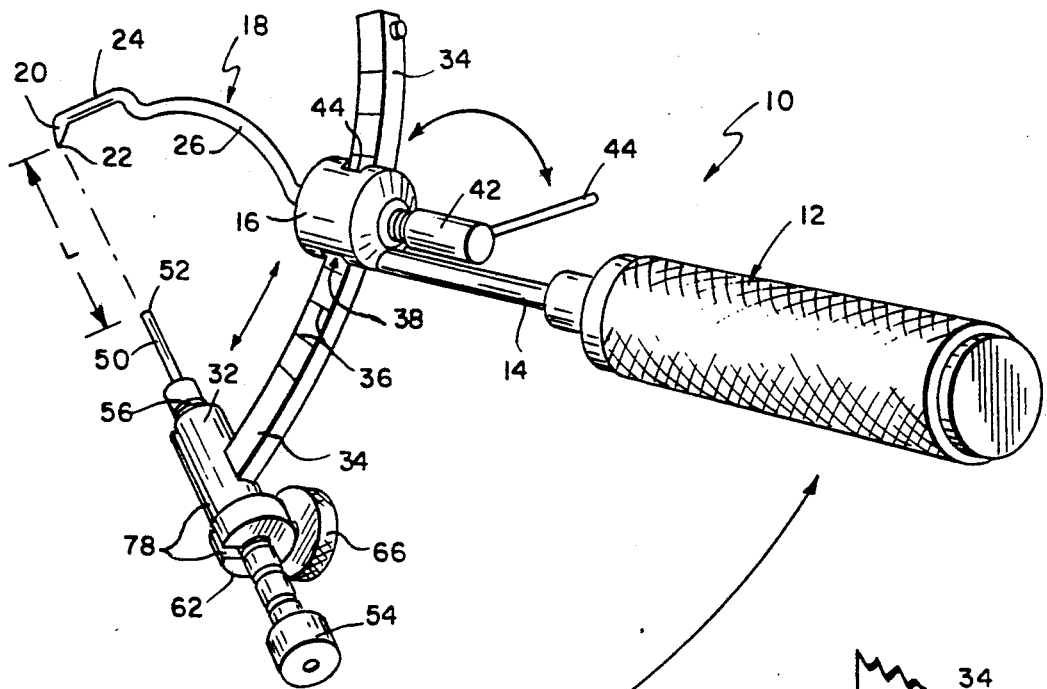
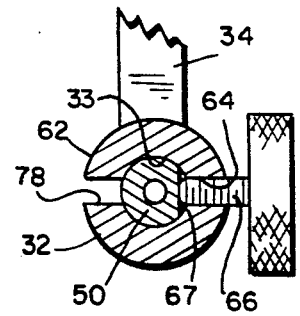
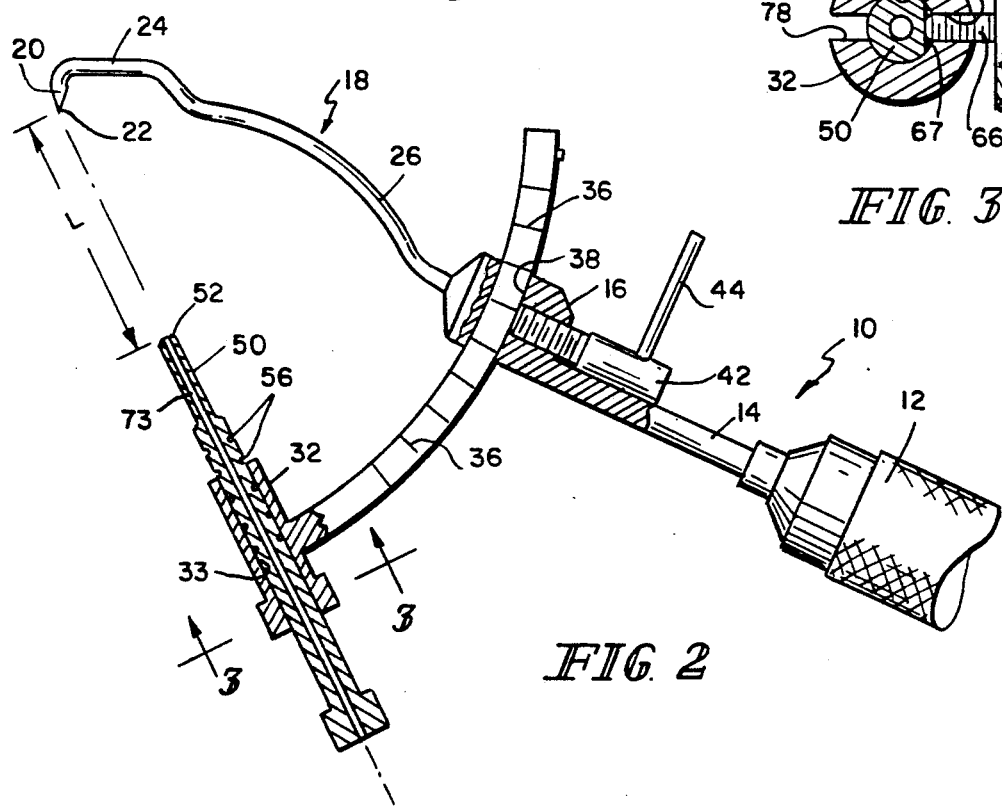

VARIABLE ANGLE, SELECTIVE LENGTH TIBIAL DRILL GUIDE

BACKGROUND OF THE INVENTION

1. Field of the Invention

The present invention relates to drill guides for accurately drilling a tunnel from the outer anterior surface of the tibia at a desired location distal to the tibial plateau upwardly through the tibia to exit at a desired location on the tibial plateau, and a method of using the drill guide for preselecting the length of the tunnel prior to any procedure which invades the bone. More specifically, the present invention relates to a tibial drill guide to facilitate an arthroscopic technique for replacing a deficient anterior cruciate ligament and a method for using the drill guide. The drill guide of the present invention includes provisions for preselecting a tibial tunnel length combined with the feature of a variable angle such that the preferred orientation of the tibial tunnel can always be achieved. In the preferred method for using the drill guide of the present invention, the preselected tunnel length is established on the drill guide and then the drill guide is manipulated to establish first the point on the tibial plateau at which the tunnel is to exit and then to vary the angle of the tunnel to find the point on the anterior medial surface of the tibia to start the drilling. Once these two points are established, with the preselected tibial tunnel length, the surgeon will know that the correct tunnel length will be achieved and that the angle of entry into the tibial plateau will be an appropriate angle.

2. The Prior Art

The prior art includes several different types of drill guides for forming tunnels in the tibia for anterior cruciate ligament replacement or enhancement. E. Marlowe Goble's U.S. Pat. No. 4,772,286 discloses a system for surgically implanting an allograft or prosthetic ligament as a replacement for a patient's cruciate ligaments. The '286 patent shows a tunnel 11 exiting the proximal tibia at a point 14 that is approximately two (2) centimeters posterior to the most anterior border of that tibial plateau 13. That point is said to be the approximate connection point of the end of the anterior cruciate ligament to the tibial bone surface. The '286 patent discloses at column 6 the use of a stainless steel guide wire to form an axis for the opening. The present invention provides a drill guide and a method for guiding the guide wire, known as a K-wire, while, at the same time, making sure that the length of the tunnel from the anterior surface of the tibia to the tibial plateau will be sufficient for the anchoring purpose desired.

The Dunbar U.S. Pat. No. 4,708,139 shows an arthroscopic drill guide, but the Dunbar guide does not have a device for preselecting the tunnel length.

Some commercial devices have a fixed angle of penetration relative to the tibial plateau such that the use of the device ends up with tunnels of uncontrolled length. Other commercial devices have fixed angles, but do have selectively variable drill sleeves to provide different tunnel lengths by choosing and installing different drill sleeves.

One commercial device has selectively variable angles with an arrangement for changing tunnel length, but there is no indicia means for rapidly establishing the preselected tunnel length. The maker of this type of device teaches setting the angle and then running up the drill sleeve until it hits bone. Thus, tunnel length is determined by the angle preselected and may vary each time.

BRIEF DESCRIPTION OF THE INVENTION

The present invention, therefore, relates to a drill guide for drilling a tunnel of preselected length in a tibia for anterior cruciate ligament replacement and a method for drilling a tunnel in a tibia for anterior cruciate ligament replacement using a drill guide. The drill guide and method are especially suited for arthroscopic surgery techniques which are now well known. The drill guide of the present invention comprises a target hook of the type having a point for engaging and determining the exit end of the tunnel in the tibial plateau, and a handle is rigidly attached to this target hook. The target hook has a downwardly extending point portion terminating with the point which engages the tibial plateau at the exit end of the tunnel, and a sight arm extending away from the point portion to be generally parallel to the tibial plateau. In use Of the guide, the sight arm is held generally parallel to the tibial plateau to orient the drill guide. The target hook also has an arch portion or a clearance portion extending outwardly from the sight arm and rigidly connected to the handle. This rigid handle, arch portion, sight arm and point portion provide the surgeon a rigid structure for locating and establishing the exit end of the tunnel and for supporting and holding the mechanism for guiding a guide wire, normally referred to as a K-wire. The handle carries a drill guide sleeve holder and selectively variable means for adjusting and rigidly fixing the angular position of the holder relative to the sight arm. The holder defines a drill axis which generally intersects the hook target point. The drill guide also comprises a drill sleeve longitudinally selectively adjustably received in the holder for axial movement toward and away from the hook guide point, the drill sleeve having indicia means longitudinally spaced therealong for selecting the position of the drill sleeve. This drill sleeve has a Proximal end extending toward the hook guide point. The drill sleeve is cannulated to receive the K-wire with a sharpened point headed toward the target hook point. Then, the holder comprises engagement means for holding the drill sleeve in a selected position, thereby preselecting the desired tunnel length between the proximal end of the drill sleeve and the target hook point.

With this drill guide, the method of the present invention comprises the steps of preselecting a desired tunnel length to accommodate the cruciate ligament replacement material and, more importantly, the fixation or anchoring mechanism or means for the replacement material. This preselected tunnel length is rigidly set by manipulating the drill sleeve holder and the engagement means to establish the selected longitudinal position of the drill sleeve in the holder. With the preselected tunnel length established, the target hook point is placed on the desired exit point of the tunnel on the tibial plateau. Then, with the sight arm on the target hook generally parallel to the tibial plateau, the angle of the holder relative to the sight arm is adjusted until the proximal end of the drill sleeve contacts a desired location on the outer, anterior surface of the tibia. This desired location is usually just medial of the tubercle. With the angle rigidly locked in position, and the proximal end of the drill sleeve in contact with the desired location on the outer anterior surface of the tibia, a pilot is drilled with the K-wire through the drill sleeve from the desired location on the anterior surface of the tibia until the point of the K-wire exits the tibial plateau adjacent the target hook point. Then, the drill sleeve may be released and axially moved away from the tibia along the K-wire. Then the holder can be removed from the K-wire and the tunnel can be drilled with a cannulated drill guided by the K-wire which remains in the tibia.

The invention provides a drill guide and method which can be used to preselect and establish the tunnel length and then to orient the angle of the tunnel within an acceptable range. It will be seen as this description progresses that the tunnel length is preselected and established by an instrument that is not present when the tunnel is drilled. Yet the tunnel will have the preselected length.

It is an object of the present invention, therefore, to provide a drill guide with a target hook and a drill sleeve holder for selectively adjustably holding the drill sleeve relative to the target hook to preselect and establish the desired tunnel length as a determining factor in locating the starting point and consequently the angle of the tunnel on the outer anterior surface of the tibia. This preselected or preestablished tunnel length is accomplished by having a drill sleeve with indicia formed longitudinally therealong for use in selecting the position of the drill sleeve. The angle of the tunnel with respect to the tibial plateau is then selectively adjusted to be within a range acceptable to the surgeon to locate the proximal end of the drill sleeve adjacent the tunnel entrance in the outer anterior surface of the tibia. The surgeon will then have a preestablished tunnel length and an angle which will provide the desired results.

Still another object of the present invention is to provide a drill guide with means for preselecting the tunnel length established on the drill guide, the said means including a drill sleeve and means for engaging and holding the drill sleeve in a selected position relative to the target hook point to establish the spacing therebetween and thereby establish the tunnel length. The present invention includes scale indicia means for indicating the distance between the proximal end of the drill sleeve and the target hook point.

A further object of the present invention is to provide such a drill guide with a holder for the drill sleeve and selectively variable means for adjusting and rigidly fixing the angular position of the holder relative to the tibial plateau. This adjusting means may include scale means for indicating the adjusted angular position of the holder about a center generally coinciding with the target hook point, and means for releasably clamping the holder in positions relative to the tibial plateau.

BRIEF DESCRIPTION OF THE DRAWINGS

FIG. 2 is a side elevational view of the present invention with portions broken away;

FIG. 3 is a sectional view taken along lines 3—3 of FIG. 1;

FIG. 4 is another perspective view of the present invention in position for introduction of the guide wire;

DESCRIPTION OF THE PREFERRED EMBODIMENT

Figure 1:
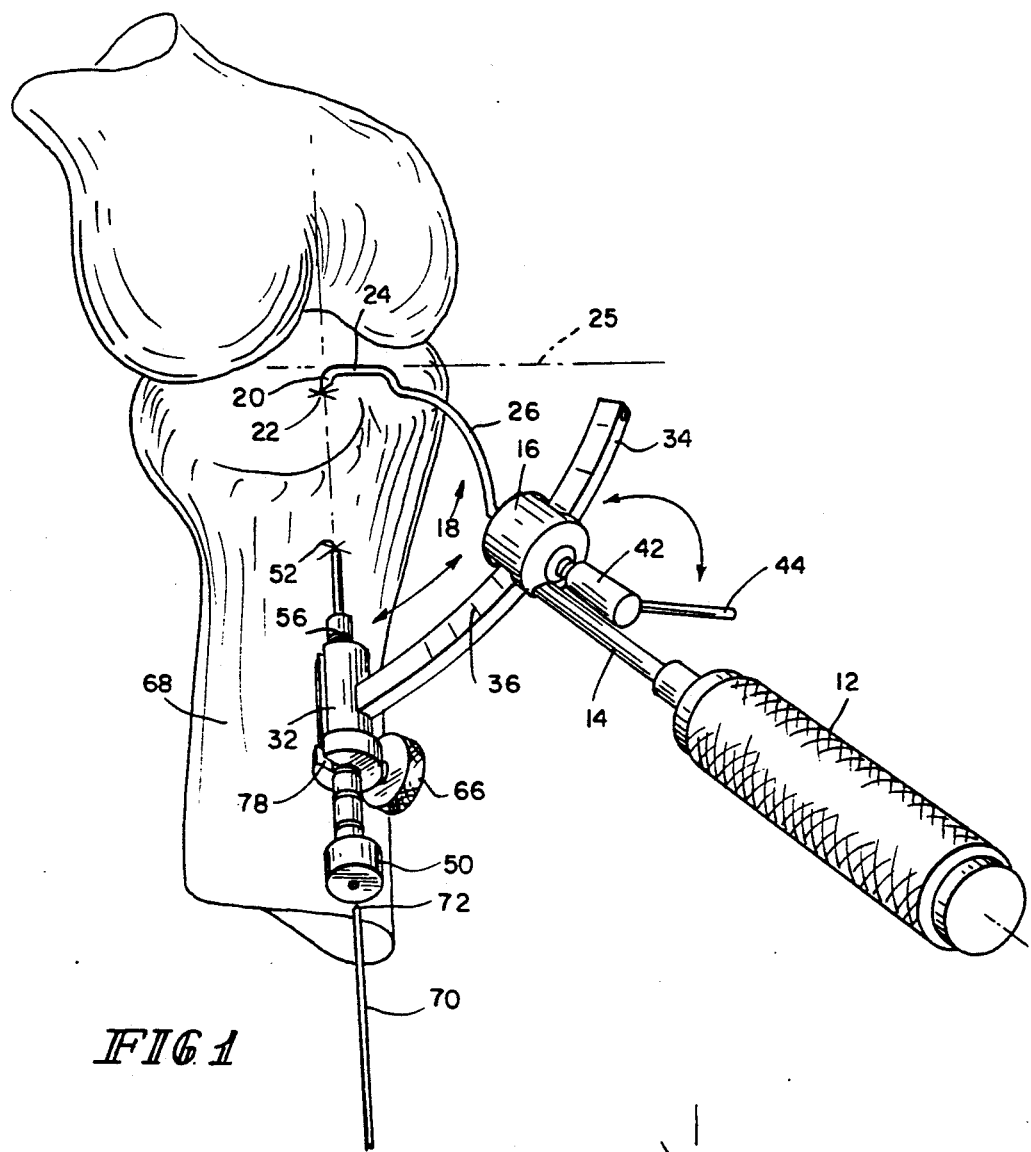
FIG. 1 is a perspective view of the present invention as would be seen looking down the handle toward the head.
Figure 5:
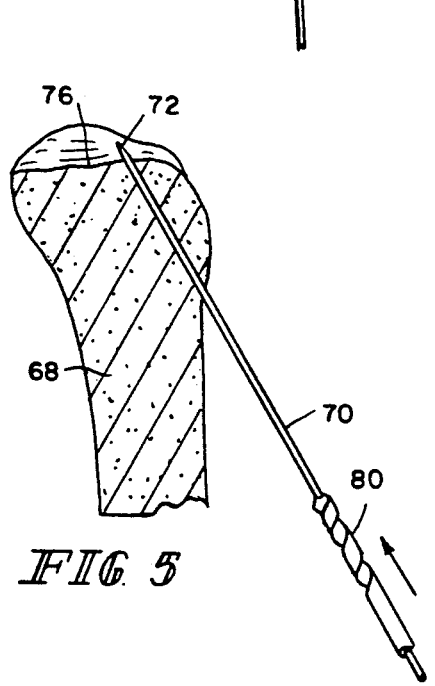
FIG. 5 is a sectional view through the tibia showing the drill guide wire in position with the tunnel drill being advanced toward the outer anterior surface.

The drill guide 10 of the present invention is illustrated to comprise a handle 12 from which extends a rigid support rod 14 to which is mounted a guide member 16. A target hook 18 with a downwardly extending target portion 20 terminating in a target hook point 22 is provided. This target hook 18 may be formed to have, for instance, a sight arm 24 extending from the upper portion of the hook portion 20 generally toward the handle 12, but in any event away from the tibial plateau. This sight arm 24, which defines a horizontal line of sight 25 generally parallel to the tibial plateau as discussed hereinafter, may be connected by an arch portion 26 to the guide member. It will be appreciated, therefore, that the illustrative drill guide 10 comprises a rigid handle, support rod, guide member and target hook all rigidly connected together to provide a reference for the parts to be discussed hereinafter. In the preferred embodiment, the handle 12, rod 14, and target hook 18 may all be formed so that their various axes lie generally in a common plane which includes the point 22.

The drill guide 10 includes a drill sleeve holder 32 which has a bore 33 defining a drill axis which, in its various positions, will generally intersect the point 22. In the illustrative embodiment, the sleeve holder 32 is adjustably connected to the guide member 16 by an arcuate slide member 34 which is formed about an axis generally intersecting the point 20. The slide member 34 may preferably have disposed thereon and spaced therealong a scale of the angular relationship between the drill axis of the holder 32 and the tibial plateau as will be discussed hereinafter. The sliding movement of the slide member 34 is through an opening 38 in the guide member 16 such that the slide member 34 generally moves in the plane defined by the axes of the handle 12, support rod 14 and target hook 18. This means that the drill axis of the holder 32 generally moves within the same plane.

The angular position of the holder 32 may be selectively fixed at any desired location by closing a screw clamp 42 which has an illustrative thumb-actuated handle 44 as best seen in the drawings. By tightening the screw clamp 42, the slide member 34 and the holder 32 can be held in any selected position.

Figure 6:
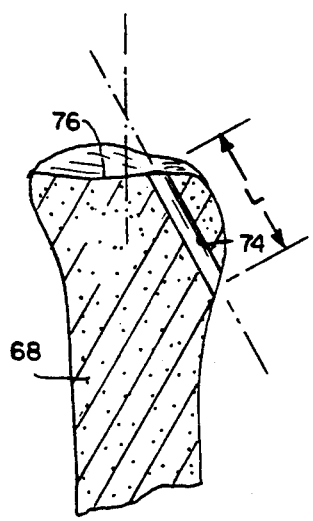
FIG. 6 is a similar sectional view illustrating the tunnel actually having a length equal to the length of the established length in FIG. 2.

The drill guide 10 also includes a drill sleeve 50 having a proximal end 52 which will contact the outer anterior surface of the tibia to locate the point at which the tunnel to be cut enters the tibia. The distance between this proximal end 52 and the point 22 will generally determine the preselected length L (FIGS. 1, 2, and 6) of the tunnel to be formed in the tibia. The drill sleeve 50 has an enlarged end stop 54 formed at one end to limit the movement of the drill sleeve toward the point 22. This stop 54, when it engages the sleeve holder 32, will limit the shortest tunnel length which can be established with the drill guide 10. For purposes of preselecting the desired tunnel length, the drill sleeve of the preferred embodiment is formed to have longitudinally spaced apart indicia 56 thereon so that the surgeon using the drill guide may quickly and efficiently preselect and set the desired tunnel length L. The indicia 56 is established such that each point therealong equals a preselected distance between the point 22 and the proximal end 52 of the sleeve 50.

The holder 32 illustratively has an enlarged end 62 into which a transverse threaded opening 64 is provided. A screw 66 with an enlarged head on it is provided for threading into the opening 64 and clamping the drill sleeve 50 in any selected longitudinal position within the holder 32. As shown in FIG. 3, the sleeve 50 has a flat 67 engaged by the screw 66. It will be seen from the description thus far, that the illustrative drill guide 10 is equipped with a holder 32 defining a tunnel drill axis which may be established at any of several different selected angles relative to the tibial plateau. In practice, as will be described in more detail hereinafter, the sight arm 24 provides a reference for positioning the handle 12 and the holder 32 relative to the tibial plateau. The sight arm 24 is held generally parallel to the tibial plateau such that movement of the holder 32 toward and away from the guide member 16 adjusts the position of the tunnel drill axis relative to the tibial plateau.

The drill guide also includes means for preselecting the position of the drill sleeve which has its proximal end 52 to contact the outer anterior surface of the tibia, thereby preselecting the tunnel length in accordance with indicia on the drill sleeve.

The drill guide 10 is set up such that once the desired exit and entrance ends of the tunnel are established, with the target hook point 22 engaging the tibial plateau at the desired location and the proximal end 52 of the drill sleeve engaging the outer anterior surface of the tibia at the desired location, a K-wire 70 with a sharpened point 72 thereon may be inserted in the drill sleeve 50 bore 73 to be driven or turned into the tibia to constitute a guide wire for later drilling the tunnel. This K-wire may be used as a guide drill wire and fed through the drill sleeve until the point 72 comes out the tibial plateau just adjacent the target hook point 22. It will be appreciated that, at this point, the K-wire will be anchored in the tibia such that the drill sleeve can be released from the holder 32 by loosening the screw 66 and pulling the drill sleeve 50 away from the tibia along the axis of the K-wire 70. This action will still leave the holder 32 about the K-wire, but the holder 32 may be provided with a longitudinally extending slot 78 through which the K-wire 70 will pass as the holder 32 is removed from the K-wire as the drill guide 10 is removed.

Once the drill guide 10 is removed leaving the K-wire anchored in the tibia, a cannulated drill may be sleeved over the outer end of the K-wire to be driven about the axis of the K-wire and forcibly into the tibia to cut the tunnel which will come out at the desired location on the tibial plateau.

The novel method of the present invention is used to assure that the tunnel will have an appropriate length L, long enough to accommodate the distal portion of the ligament replacement to be placed therein and any fixation device that may be used. The method, therefore, is a method for drilling a tunnel 74 in a tibia for anterior cruciate ligament replacement using the drill guide 10 comprising the target hook 18 having a point 22 for engaging and determining the exit end of the tunnel 74 in the tibial plateau 76. The method comprises the steps of preselecting the desired tunnel length L defined between the proximal end 52 of the drill sleeve 50 and the target hook point 22. This is accomplished by rigidly setting the drill sleeve 50 in the holder 32 by clamping the sleeve with the clamping screw 66 at the desired location shown by the indicia 56. Once the preselected tunnel length L is established by fixing the position of the drill sleeve 50 in the holder 32, the target hook point 22 is engaged at the desired exit point of the tunnel on the tibial plateau, this point generally being the point at which the anterior cruciate ligament originates on the tibial plateau. Then, the angle of the holder 32 is adjusted relative to the sight arm 24 or relative to the tibial plateau until the proximal end 52 of the drill sleeve 50 contacts a desired location on the outer anterior surface of the tibia. This desired location will generally be just medial of the tubercle on the outer anterior surface of the tibia as shown in the drawing FIG. 4. At this point, after that angle is adjusted and established, a pilot hole may be drilled with a K-wire through the drill sleeve from the desired location on the anterior surface of the tibia until the point of the K-wire 70 exits the tibial plateau 76 adjacent the target hook point 22. Once the K-wire is anchored in the tibia, the drill sleeve 50 may be released from the holder 32 and removed axially away from the tibia along the K-wire 70. Once the sleeve 50 is removed, the holder 32 can be removed from the K-wire 70 by the slot 78. Then a tunnel may be drilled with a cannulated drill 80 guided by the K-wire which remains in the tibia.

What is claimed is:

1. A drill guide for drilling a tunnel in a tibia for anterior cruciate ligament replacement comprising a target hook having a point for engaging and determining the exit of the tunnel in the tibial plateau, a handle rigidly attached to the target hook, said target hook having a downwardly extending point portion terminating with said point, a sight arm extending away from the point portion to be generally parallel to the tibial plateau, and an arch portion extending back from the sight arm and rigidly connected to said handle, said handle carrying a drill guide sleeve holder and selectively variable means for adjusting and rigidly fixing the angular position of said holder relative to the sight arm, said holder defining a drill axis which generally intersects said point, said drill guide also comprising a drill sleeve longitudinally selectively adjustably received in said holder for axial movement toward and away from said point, said drill sleeve having indicia means longitudinally spaced therealong for selecting the position of said drill sleeve, said drill sleeve having a proximal end extending toward said point, said drill sleeve being cannulated to receive a guide wire with a sharpened point headed toward said target hook point, and said holder comprising engagement means for holding said drill sleeve in a selected position, thereby Preselecting the desired tunnel length defined between said proximal end of said drill sleeve and said target hook point, such that placing said target hook point on the desired exit point of the tunnel and then adjusting the angle of said holder relative to said sight arm until the proximal end of said drill sleeve contacts a desired location on the outer anterior surface of the tibia will position the guide wire for penetrating movement through the drill sleeve from said desired location on the anterior surface of the tibia to the tibial plateau adjacent said target hook point.

2. The drill guide of claim 1 in which said drill guide sleeve holder has a longitudinally extending slot throughout its length through which said guide wire may move transaxially relative to said holder to remove said holder from said guide wire after said drill sleeve is removed axially from said guide wire and said holder.

3. The drill guide of claim 1 in which said drill sleeve is provided with an enlarged axially outer end portion to engage said drill guide sleeve holder to serve as a stop limiting the movement of said proximal end of said drill sleeve toward said target hook point.

4. The drill guide of claim 3 in which said engagement means for holding said drill sleeve in a selected position includes fastening means carried by said drill guide sleeve holder to engage and hold said drill sleeve.

5. The drill guide of claim 4 in which said selectively variable means for adjusting and rigidly fixing the angular position of said drill guide sleeve holder includes a slide member which is arcuately formed about an axis generally intersecting said point and to which is rigidly attached said guide sleeve holder, a guide member carried by said handle, said guide member having an opening through which said slide member moves, and fastening means for holding said slide member relative to said guide member.

6. The drill guide of claim 5 in which said fastening means for holding said slide member is positioned to be actuated by the thumb of the hand holding said handle.

7. The drill guide of claim 6 in which said drill guide sleeve holder has a longitudinally extending slot throughout its length through which said guide wire may move transaxially relative to said holder to remove said holder from said guide wire after said drill sleeve is removed axially from said guide wire and said holder.

8. A drill guide for drilling a tunnel of preselected length in a tibia for anterior cruciate ligament replacement comprising a target hook having a point for engaging and determining the exit of the tunnel in the tibial plateau, a handle rigidly attached to the target hook, said target hook having a downwardly extending point portion terminating with said point and a sight arm extending away from the point portion to be generally parallel to the tibial plateau, a drill guide sleeve holder, selectively variable means for adjusting and rigidly fixing the angular position of said holder relative to the sight arm, said holder defining a drill axis which generally intersects said point, said adjusting means including a curved slide member arcuately formed about a center generally coinciding with said target hook point, indicia means disposed on said slide member and spaced therealong to indicate the angular position of said holder, a guide member for engaging said slide member, and means for clamping said slide member in a fixed position relative to said guide member, a drill sleeve longitudinally selectively adjustably received in said holder for axial movement toward and away from said target hook point, said drill sleeve having indicia means longitudinally spaced therealong for selecting the position of said drill sleeve, said drill sleeve having a proximal end extending toward said point such that the selected distance between said proximal end and said target hook Point determines length of the tunnel, said drill sleeve being cannulated to receive a guide wire with a sharpened point headed toward said target hook point, and said holder including engagement means for holding said drill sleeve in a selected position, thereby preselecting the desired tunnel length.

9. A drill guide for drilling a tunnel of preselected length in a tibia for anterior cruciate ligament replacement comprising a target hook having a point for engaging and determining the exit of the tunnel in the tibial plateau, a handle rigidly attached to the target hook, a drill guide sleeve holder, selectively variable means for adjusting and rigidly fixing the angular position of said holder relative to the tibial plateau, said holder defining a drill axis which generally intersects said point, said adjusting means including scale means for indicating the adjusted angular position of said holder about a center generally coinciding with said target hook point, and means for releasably clamping said holder in positions relative to said target hook point, a drill sleeve longitudinally selectively adjustably received in said holder for axial movement toward and away from said target hook point, said drill sleeve having a proximal end extending toward said point for contacting the outer anterior surface of the tibia at a desired location for starting the tunnel, said drill sleeve being cannulated to receive a guide wire with a sharpened point headed toward said target hook point, means for clamping said drill sleeve in a selected position on said holder, thereby preselecting the desired tunnel length, and scale indicia means for indicating the distance between said proximal end of said drill sleeve and said target hook point to indicate the preselected tunnel length.

10. A method for drilling a tunnel in a tibia for anterior cruciate ligament replacement using a drill guide comprising a target hook having a point for engaging and determining the exit of the tunnel in the tibial plateau, a handle rigidly attached to the target hook, said target hook having a downwardly extending point portion terminating with said point, a sight arm extending away from the point portion to be generally parallel to the tibial plateau, and an arch portion extending back from the sight arm and rigidly connected to said handle, said handle carrying a drill guide sleeve holder and selectively variable means for adjusting and rigidly fixing the angular position of said holder relative to the sight arm, said holder defining a drill axis which generally intersects said point, said drill guide also comprising a drill sleeve longitudinally selectively adjustably received in said holder for axial movement toward and away from said point, said drill sleeve having indicia means longitudinally spaced therealong for selecting the position of said drill sleeve, said drill sleeve having a proximal end extending toward said point, said drill sleeve being cannulated to receive a guide wire with a sharpened point headed toward said target hook point, and said holder comprising engagement means for holding said drill sleeve in a selected position, thereby preselecting the desired tunnel length defined between said proximal end of said drill sleeve and said target hook point, said method comprising the steps of preselecting a desired tunnel length and rigidly setting said drill sleeve position in said holder with said engagement means to establish the tunnel length, then placing said target hook point on the desired exit point of the tunnel, then adjusting the angle of said holder relative to said sight arm until the proximal end of said drill sleeve contacts a desired location on the outer anterior surface of the tibia, then drilling a pilot hole with the guide wire through the drill sleeve from said desired location on the anterior surface of the tibia until the point of the guide wire exits the tibial plateau adjacent said target hook point, then removing the drill sleeve axially rearwardly away from the tibia along the guide wire, removing the holder, and drilling the tunnel with a cannulated drill guided by the guide wire which remains in the tibia.

11. A method for drilling a tunnel of preselected length in a tibia for anterior cruciate ligament replacement using a drill guide comprising a target hook having a point for engaging and determining the exit of the tunnel in the tibial plateau, a drill guide sleeve holder and selectively variable means for adjusting and rigidly fixing the angular position of said holder relative to the tibial plateau, said holder defining a drill axis which generally intersects said target hook point, a drill sleeve longitudinally selectively adjustably received in said holder for axial movement toward and away from said target hook point, said drill sleeve having indicia means longitudinally spaced therealong for selecting the position of said drill sleeve, said drill sleeve having a proximal end extending toward said point, said drill sleeve being cannulated to receive a guide wire with a sharpened point headed toward said target hook point, and said holder comprising engagement means for holding said drill sleeve in a selected position, thereby preselecting the desired tunnel length defined between said proximal end of said drill sleeve and said target hook point, said method comprising the steps of preselecting a desired tunnel length and rigidly setting said drill sleeve position in said holder with said engagement means to establish the tunnel length, then placing said target hook point on the desired exit point of the tunnel, then adjusting the angle of said holder relative to said tibial plateau until the proximal end of said drill sleeve contacts a desired location on the outer anterior surface of the tibia, then drilling a pilot hole with the guide wire through the drill sleeve from said desired location on the anterior surface of the tibia until the point of the guide wire exits the tibial plateau adjacent said target hook point, then removing the drill sleeve axially rearwardly away from the tibia along the guide wire, removing the holder, and drilling the tunnel with a cannulated drill guided by the guide wire which remains in the tibia.

* * * * *